United States Patent [19]

Cox et al.

[11] Patent Number: 4,562,846

[45] Date of Patent: Jan. 7, 1986

[54] SYSTEM AND PROCESS FOR MONITORING MYOCARDIAL INTEGRITY

[75] Inventors: James L. Cox, St. Louis, Mo.; T. Bruce Ferguson, Jr.; Gary K. Lofland, both of Durham, N.C.; Barry Branham, St. Louis, Mo.

[73] Assignee: Duke University, Durham, N.C.

[21] Appl. No.: 532,383

[22] Filed: Sep. 15, 1983

[51] Int. Cl.⁴ .............................................. A61B 5/04
[52] U.S. Cl. ................................................... 128/696
[58] Field of Search ............... 128/640, 642, 421–423, 128/419 D, 696, 700, 702, 704–705, 708, 710

[56] References Cited

U.S. PATENT DOCUMENTS

| | | | |
|---|---|---|---|
| 3,313,293 | 4/1967 | Chesebrough et al. | 128/642 |
| 3,590,811 | 7/1971 | Harris | 128/708 |
| 3,853,119 | 12/1974 | Peterson et al. | 128/708 |
| 3,884,221 | 5/1975 | Eastman | 128/699 |
| 3,939,824 | 2/1976 | Arneson et al. | 128/708 |
| 4,068,310 | 1/1978 | Friauf | 128/710 |
| 4,172,451 | 10/1979 | Kline | 128/642 |
| 4,364,397 | 12/1982 | Citron et al. | 128/710 |
| 4,393,877 | 7/1983 | Imran et al. | 128/705 |
| 4,463,425 | 7/1984 | Hirano et al. | 128/704 |

FOREIGN PATENT DOCUMENTS

| | | | |
|---|---|---|---|
| 2143971 | 3/1973 | Fed. Rep. of Germany | 128/704 |
| 2413941 | 10/1974 | Fed. Rep. of Germany | 128/708 |
| 2340588 | 10/1977 | France | 128/696 |

OTHER PUBLICATIONS

Taunton et al., "Solid State Delay Unit for a Cardiac Arrythmia Monitor", J Med Eng & Technol (GB) vol. 3, No. 1, Jan. 1979, pp. 29–30.

Primary Examiner—William E. Kamm
Assistant Examiner—Mitchell J. Shein
Attorney, Agent, or Firm—Oblon, Fisher, Spivak, McClelland & Maier

[57] ABSTRACT

A process and apparatus for providing an electrophysiologic indicator of reversible myocardial ischemic injury as well as a procedure and apparatus for providing a method of assessing the status of myocardial preservation during elective cardioplegic arrest in order to assure complete electromechanical arrest from the onset of the application of the standard cardioplegic techniques. The procedure for establishing an indication of reversible myocardial ischemic injury involves implanting multiple electrodes in the myocardial tissue and sensing the instantaneous unipolar electrical potentials of the electrodes and comparing those sensed potentials with a series of registered potentials for healthy tissue. The procedure and apparatus for assessing the status of myocardial preservation involves the use of the same implanted multiple electrodes which are placed in the ventricle and the apparatus provides for a sensing and documenting of ventricular electrical activity in the visually arrested heart at a time when a peripheral EKG would be quiescent in order to detect persistent activity originating in the lower atrial septum and conducted through the AV node to the ventricles at what was previously considered to be safe myocardial temperatures.

10 Claims, 10 Drawing Figures

SYSTEM AND PROCESS FOR MONITORING MYOCARDIAL INTEGRITY

BACKGROUND OF THE INVENTION

1. Field of the Invention

The present invention relates to the intraoperative and postoperative monitoring of cardiac surgery patients by establishing and monitoring electrophysiologic parameters to determine myocardial ischemic injury during and after cardiac surgical procedures.

2. Description of the Prior Art

The current sophisticated techniques which have led directly to improved care and treatment of patients during and after cardiac surgery have been provided without a reliable technique being available to monitor the viability and integrity directly of the myocardium either during or after cardiac surgery.

Myocardial ischemic injury may occur at any time during perioperataive periods in patients who are undergoing cardiac surgical procedures. This period of time when surgery is ongoing and when treatment is ongoing after surgery, is filled with the dangers of hypotension secondary to the general anesthetic agent employed. The intraoperative period is characterized by intensive efforts to maintain a satisfactory relationship between myocardial supply and myocardial demand during cardiopulmonary bypass using a wide variety of techniques for myocardial preservation. During the postoperative period, attention is primarily directed towards maintaining an adequate cardiac output by employing various types of pharmacologic and mechanical therapeutic support.

The methods currently used to determine the adequacy of the myocardial preservation during cardiopulmonary bypass are capable of detecting myocardial injury only after it is too late to reverse the injury. Likewise, although it is possible to monitor the status of the lungs, brain, kidneys, blood components, and coagulation factors during and after cardiac surgery, no reliable technique is available to assess myocardial integrity. Therefore, it has been the experience of most cardiac surgeons who have performed a cardiopulmonary bypass which has been smoothly initiated and carried through to have experienced instances during which an apparently uncomplicated technical operation with "good myocardial preservation" has been followed by an inability of the myocardium to generate a contractile force which is adequate to allow termination of cardiopulmonary bypass.

With regard to the area of anesthetics, a similar situation has arisen to that of the mycardial integrity observed concerning a normal bypass. That is, despite statistically acceptable operative mortality figures, electrocardiographic changes and serum isoenzyme levels consistent with intraoperative myocardial infarction may be present in as many as 25% of patients undergoing cardiac surgery. Thus far the major effort at preventing perioperative myocardial injury has centered on the intraoperative period. This goal of myocardial preservation has currently been based upon a simple observation that if the myocardium can be maintained in its pre-bypass state during the period of cardiopulmonary bypass, it should maintain that prebypass state after cessation of cardiopulmonary bypass. Intermittent aortic cross-clamping, selective coronary perfusion when associated with valvular surgery, induced ventricular fibrillation, hypothermia, and potassium cardioplegia have been previously employed to "preserve" the myocardium during the cardiopulmonary bypass.

Concerning the improvements which have recently been made to postoperative pharmacological methods and treatments such as nitroprusside and Dopamine, it is to be noted that while they have made control of cardiac output much easier during the first critical hours and days following cardiac surgery, they do not leave the domain of emperical studies because the immediate effect of the various drugs on myocardial integrity is unknown.

Another area of concern with regard to myocardial integrity exists during the cardiopulmonary surgery when an electrocardioplegic arrest has been effected. The concept of elective cardioplegic arrest for myocardial preservation involves the electrical and mechanical arrest of the heart through the use of various clamping techniques and the infusion of a cardioplegic solution. Continuous monitoring of ventricular septal temperature has been used to improve the surgeon's ability to determine the optimal time to re-infuse cardioplegic solution when the period of cardioplegic arrest is prolonged. Electrical arrest is commonly documented by continuous monitoring of a peripheral limb-lead electrocardiogram and the mechanical arrest is verified by visual inspection. Aside from these two observations with regard to monitoring of the activity of the heart the only other assurance given to a surgeon of the complete arrest of the heart has been the re-perfusion with the cardioplegic solution at predetermined time periods. These predetermined time periods are based on empirical observations with regard to the length of time a normal heart is "quiet" after the initial infusion of the solution. There is no other, more accurate, determination with regard to the assurance of the complete inactivity of the heart during the progress of the operation. Because the energy requirements of the myocardium are greater when any activity is occurring, the previous methods of determining electrical and mechanical arrest lack a sufficient observable basis for concluding inactivity in the heart with respect to preserving myocardial integrity.

Despite all of these recent advances in myocardial preservation, the emphasis for improvement has been markedly fixed on determining which technique is the best or most effective. It has been demonstrated that any of the above-mentioned techniques is adequate in a particular patient and that none of the techniques is adequate in all of the patients. This leaves the field with a critical need for a means to determine during cardiopulmonary bypass the exact point in time when myocardial preservation becomes inadequate, regardless of the technique employed. Standard electrocardiographic changes, serum isoenzyme changes, and postoperative cardiac function analysis are capable of indicating the adequacy of intraoperative myocardial preservation only in a retrospective manner. Likewise, as indicated above, potential harmful effects of postoperative pharmacological agents on the myocardium of a given patient can be detected only after these effects have occurred.

SUMMARY OF THE INVENTION

Accordingly, one object of the present invention is to provide a novel procedure which is directed toward establishing an electrophysiologic indicator of reversible myocardial ischemic injury which involves the implantation of multiple electrodes in the myocardial tissue and sensing the instantaneous unipolar electrical potentials of the electrodes and comparing those sensed potentials with a series of registered potentials for healthy tissue.

It is another object of the invention to provide a method of assessing the status of myocardial preservation during cardioplegic arrest in order to assure complete electromechanical arrest from the onset of the application of the standard cardioplegic techniques. The process involved in this improved monitoring involves the use of intramural electrodes placed in the ventricular and the use of recording apparatus for documenting ventricular electrical activity in the visually arrested heart at a time when the peripheral EKG was quiescent in order to detect persistent activity originating in the lower atrial septum and conducted through the AV node to the ventricles at what was previously considered to be safe myocardial temperatures. This continuous monitoring of intramural electrical activity provides a more reliable technique than the prior art for determining the adequacy of myocardial preservation during elective cardioplegic arrest.

It is a further object of the present invention to provide a monitoring system which displays the viability of myocardial tissue and which employs a plurality of electrodes which are suitable for implantation in the myocardial tissue with the output of the electrodes being sensed for their instantaneous electrical potentials. The system further compares the instantaneous electrical potentials with previously registered normal electrical potentials in order to provide to a display device the results of the comparison which are indicative of the viability of the myocardial tissue in which the electrodes are implanted.

The monitoring system for monitoring and displaying the viability of myocardial tissue is easily modified to provide a monitoring system for detecting the occurrence of any persistent electrical activity occurring during elective cardioplegic arrest in order to provide an indication as to the adequacy of myocardial preservation during the cardioplegic arrest procedure.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
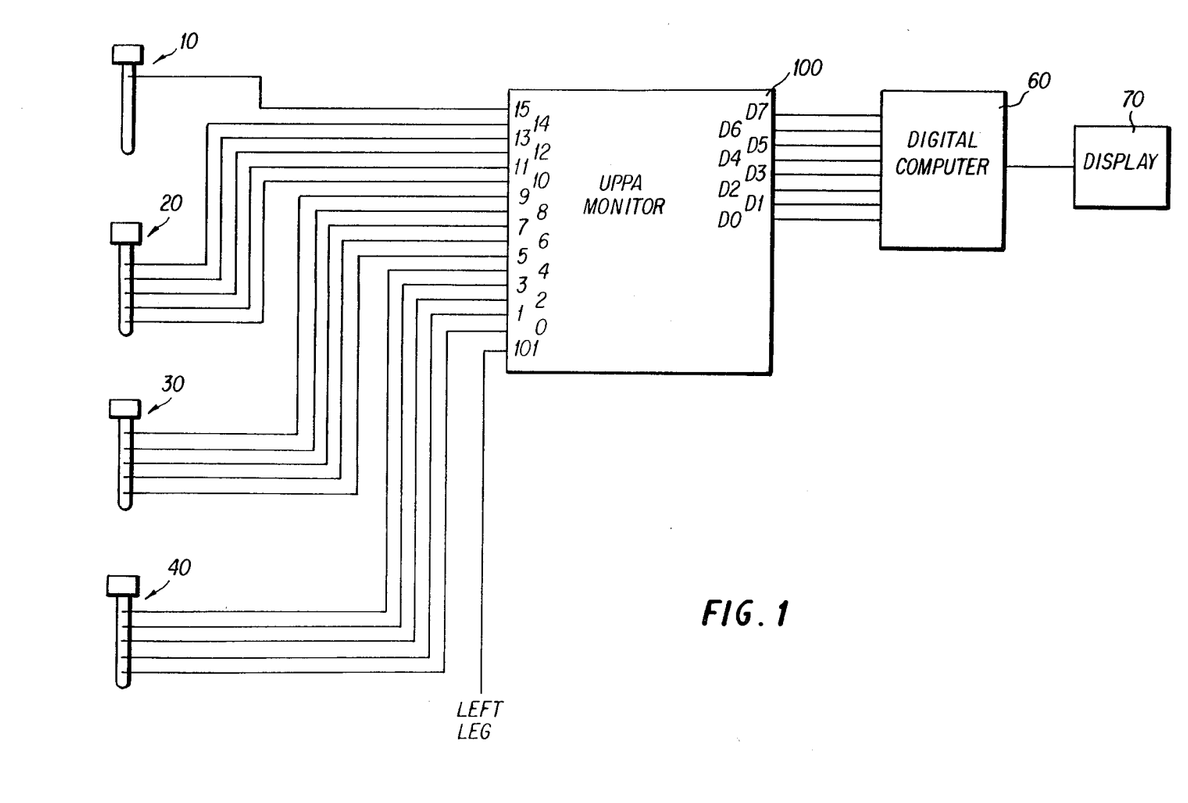
FIG. 1 is a block diagram of the electrophysiologic data acquisition system including an UPPA monitor showing the connection to plunge electrodes.
Figure 2A:
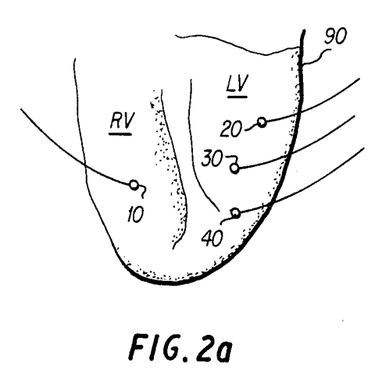
FIGS. 2a and 2b illustrate the intramural placement of the plunge electrodes and the structure of the contacts of one of the plunge electrodes.
Figure 2B:
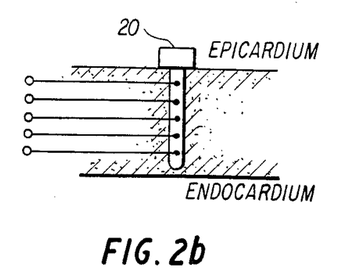
Figure 3:
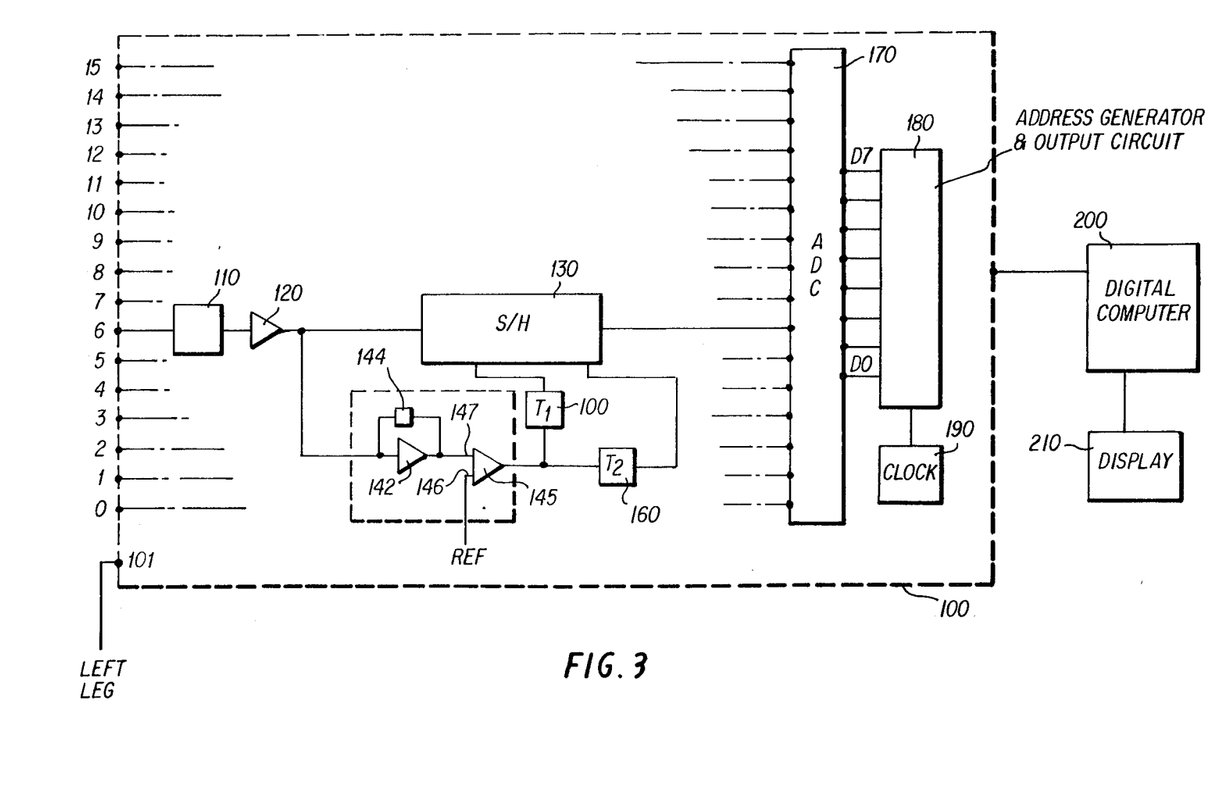
FIG. 3 is a detailed block diagram of the construction of the UPPA monitor of the data acquisition system of the FIG. 1.

Referring now to the drawings, wherein like reference numerals designate identical or corresponding parts throughout the several views, and more particularly to FIGS. 1–3 thereof, there is shown the apparatus for practicing the process whereby the status of the left ventricular myocardium is monitored in an on-line fashion during intraoperative and postoperative periods such that at any given instant multiple sites throughout the left ventricular myocardium can be assessed for damage.

The procedure in monitoring each patient involves the placement of four plunge electrodes 10–40 into the heart of the patient whereby the reference electrode 10 is placed in the left ventricular. The plunge electrode 20 is placed into the anterior left ventricular while the electrode 30 is placed into the lateral left ventricular and the electrode 40 is placed into the posterior left ventricle. Each of the plunge electrodes 20, 30 and 40 contain 5 unipolar contact points spaced one millimeter apart along the shaft of the 0.22-gauge plunge needles.

The placement of these electrodes and the types of electrodes as well as the accompanying measurement system have been designed with a view toward detecting myocardial ischemic injuries based on electrophysiologic changes sufficiently early to allow therapeutic intervention to alleviate or prevent permanent damage.

Myocardial ischemic injury may occur at any time during the perioperative period in patients undergoing cardiac surgical procedures. The induction period provides many dangers including hypotension which are secondary to the general anesthetic agent employed. This intraoperative period is characterized by intensive efforts to maintain a satisfactory relationship between myocardial supply and myocardial demand during the cardiopulmonary bypass using a wide variety of techniques for myocardial preservation.

It has been found that certain electrophysiologic parameters can be correlated with local myocardial blood flow, metabolism and histology so that the electrophysioligic changes will have exact prognostic implications upon their detection and once these implications are found then therapeutic or surgical action can be taken to provide correction or relief. Among the electrophysiologic data studied, the S-T wave changes, the Q-wave alterations, the unipolar action potential amplitude, bipolar action potential amplitude and local activation type have been studied in numerous instances with a view toward providing an indication of ischemic injury by means of the measurement of these electrical outputs from the heart beat phenomenon occurring throughout the myocardial tissue.

The parameter which has been found to provide a very close correlation between the reversibility of the myocardial ischemic injury and the measurement of that parameter is called the unipolar peak-to-peak amplitude (UPPA) and is a measurement of the rapid intrinsic deflection which represents local tissue activation. It is, in electrical terms, the first rapid negative deflection recorded from each intramural contact point of which there are five for each of the electrodes 20, 30 and 40 in the left ventricle as shown in the drawings. As previously indicated, these contact electrodes are located and placed so as to be one millimeter apart thereby providing an indication in the form of an electrical signal to the UPPA monitor 100 for each of the intramural contact points. In order to distinguish between electrical activity occurring, in the myocardial tissue between the intramural electrodes, which is not of interest the monitoring system including the UPPA monitor is constructed so that only the first occurring rapid negative deflection is detected. This deflection must exceed 2 millivolts per millisecond in order to be detected as a UPPA by the monitoring system 100. The system is also designed to measure the peak-to-peak voltage from each of these 16 intramural contact point (15 from the three plunge electrodes 20, 30 and 40 and 1 from the reference plunge control electrode).

The electrograms which were studied in order to obtain the observation with regard to the UPPA voltage were brought about as the result of electrograms which were recorded from the specific subepicardial contact points on the same plunge electrode which were seen to maintain their amplitude above the level of 70% of a reference value for normally healthy tissue throughout a period of time. If an individual intramural electrogram demonstrated a decrease in its unipolar action potential amplitude (UPPA) so that it was 70% or less of the control amplitude for healthy tissue at any time during the coronary occlusion, the histological studies which were conducted later on the particular tissue which surrounded the intramural contact showed that the myocardium immediately adjacent to that intramural contact point was infarcted. All electrograms which were recorded from a plunge electrode passed through a transmural myocardial infarction showed a decrease in its unipolar action potential amplitude (UPPA) to less than 70% of the control amplitude for normally healthy tissue. All examples of tissue study where the UPPA recorded did not fall below 90% of the control amplitude revealed that no permanent histologic damage had occurred. There was a normal biologic variation in permanent myocardial damage if the UPPA fell to between 70% and 90% of the control UPPA. Thus the conclusion is that a decrease in the unipolar action potential amplitude below 70% for normally healthy tissue, or in other words for a control amplitude, indicates myocardial ischemic injury and more particularly indicates irreversible ischemic injury in all instances.

The histologic data was obtained by evaluating tissue samples obtained from the myocardium surrounding each intramural plunge electrode and its electrode contacts. All intramural plunge electrodes were dipped in India ink prior to implantation in the myocardium so that the exact location of each wire was identified histologically. Because the distance between adjacent electrode terminals was known and because the endocardial and epicardial contacts on each plunge electrode are obvious from the control electrograms, histologic examinations of the tissue lying in direct contact with each intramural electrode was possible. This provided for accurate correlation between the electrophysiological and the histologic data from precisely the same area of the myocardium. The histologic changes were evaluated through the use of the normal techniques in this area including the use of Hematoxylin and eosine (H and E), phosphotungstic acid hematoxylin (PTAH), and Succinic dehydrogenase (SDH) enzyme stains.

Once the indices such as the UPPA were provided and validated, numerous pharmacologic and mechanical interventions to improve areas of myocardial ischemic entry can be studied through the use of this technique in order to provide a beneficial treatment. These areas could include potential benefits from coronary vasodilators, beta blocking agents, pharmacologically decreased afterload, cardiac symphthectomy, intraaortic balloon pumping, and others.

Based upon these experiments and the validated results including the primary result that the UPPA measurement, as obtained, provides an indication of ischemic injury based upon a 70% maintenance of the normal level, the monitoring system including the UPPA monitor 100 was designed and can effectively be used with regard to patients during the intraoperative and postoperative periods of time to provide an indication of a need for further treatment without awaiting for the developments of secondary indications of problems which may occur too late to effectively take corrective surgical or therapeutic action.

The measurement of the UPPA voltages and the resultant manipulation of the voltages from the 16 intramural contacts is accomplished through the use of a programmed Digital Computer 60 which receives the output of the UPPA monitor 100 and correlates the information to provide an output to a display 70 which is indicative of problem areas within the patient either occurring during an operation or immediately thereafter for a period to be determined by a physician with regard to each particular patient.

The FIG. 3 details the construction of the UPPA monitor 100 by showing effectively one of the 16 channel signal processing units in detail with each of the remaining 15 channels being identical. An input signal from one of the contact points of a needle unipolar electrode is fed as shown in FIG. 3 to an imput numbered 6 through an isolation amplifier 110 and a follower amplifier 120. The gain of the unit is adjusted by adjusting the gain of the follower amplifier 120. The output of the follower amplifier is fed both to a sample and hold circuit 130 and to a slope detector circuit 140. The slope detector 140 has for its purpose the detection of a negative going potential which exceeds 2 millivolts per milliseconds. If such a signal does not exist, then no signal is output to the analog digital converter 170.

The sample and hold circuit comprises a differential circuit 142 having a feedback 144 with the output of the differential circuit being fed to one input 147 of a comparator 145 while the other input 146 of the comparator 145 is fed with a reference voltage which is used to determine the basis of comparison for example and providing a signal to be passed through which has a slope of greater than 2 millivolts per milliseconds. The output of the slope detector circuit 140 is fed through a first timing delay circuit 150 which is set at 1.5 milliseconds and provides for blocking of a subsequent retrigering of the sample and hold circuit 130 during that time period. The delay circuit T$_2$ labeled 160 provides that the output of the sample and hold circuit is delayed by 150 milliseconds to provide for continued digitization of signals after the first occurring signal.

Once the signal has been sampled and held in the circuit 130 and once the slope detector has qualified the signal as a signal able to be passed through and once that signal indicator has been delayed by the appropriate time period, the output of the sample and hold circuit 130 is fed to one of the channels of an analog to digital converter 170. Each of the 16 parallel input channels to the analog to digital converter 170 is converted into a serial-parallel output of 8 bits. That is, the output is read out in a serial fashion with each of the parallel outputs d0-d7 representing an 8 bit binary word indicating a value for the voltage read by the particular contact point. This output information is fed to an address generator 180 which is controlled by clock 190 in order to provide information with regard to the particular channel which is being read out at any one particular time. The address generator circuit also includes an output circuit which converts the information and its associated channel to a signal form which can be used by the digital computer 200. This output format may be for example a RS232 output or any other of a number of outputs which can be interfaced with a digital computer.

The digital computer 200 is programmed in order to provide information with regard to areas included between the various electrodes which may indicate irreversible injury. Normal values are ascertained from the patient prior to beginning the surgical procedures in order to provide comparison value for the later values which are obtained during the procedure itself and during postoperative recovery. These normal values are used to provide the basis for indicating when any of the values fall below the 70% level as an indication of ischemic irreversible injury. The output 210 may provide any one of a number of displays indicating areas of possible injury to myocardial tissue either on an individual contact basis or on some mapping array which indicates a positioning of the contacts and the areas where the injury has occurred.

The UPPA monitor 100 is constructed so that a grounding reference shown at 101 provides a grounding source for each of the outputs of the unipolar plunge electrodes 10, 20, 30 and 40 with this grounding electrode being connected to the left leg of the patient in a manner similar to an electrocardiogram reading.

While the procedure and the system described above function well in determining myocardial injury at all times during and after a cardiac surgical procedure except during the period of cardioplegic arrest, this particular monitoring of the UPPA voltage has no relevance during the period of cardioplegic arrest because all activity both electrical and mechanical is halted which is the purpose of the cardioplegia itself. Although numerous advances have been made in the application of cardioplegic techniques, the continuous monitoring of the ventricular septal temperature has been the major factor used to improve the surgeon's ability to determine the optimal time to re-infuse cardioplegic solution when the period of cardioplegic arrest is prolonged. The electrical arrest of the heart is commonly documented by continuous monitoring of a peripheral limb-lead electrocardiogram and the mechanical arrest is verified by visual inspection only. It has been observed during the course of experimental studies that ventricular electrical activity may occur during the period of cardioplegic arrest and might not be detected by the standard limb-lead electro-cardiogram.

Because of the design of the UPPA monitor 100 and the associated system as illustrated in FIGS. 1–3 the monitor 100 itself has been designed so that it can be easily modified to provide an indication of any electrical activity occurring in the left ventricular during the period of elective cardioplegic arrest. It appears quite certain that the significance of any type of intramural electrical activity during cardioplegic arrest has a direct correlation with further requirements for postoperative pharmacological and mechanical support. The type of activity detected by the monitor 100 and the associated system as modified provides an indication of electrical activity which has been previously undetected and which, as will be seen, is an immediate and reliable indicator of the need for intraoperative action on the part of the operating team who would previously have no indication of a possible problem with regard to electrical activity occurring within the heart during the period of elective cardioplegic arrest.

Figure 4:
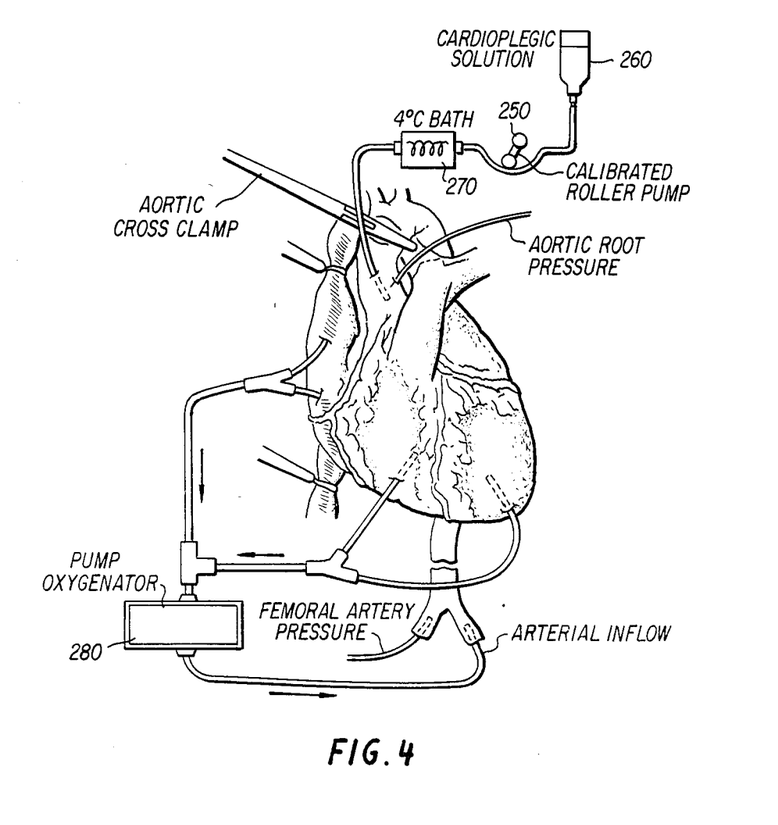
FIG. 4 illustrates a typical preparation of the heart for elective cardioplegic arrest.

The FIG. 4 illustrates a preparation of a heart for elective cardioplegic arrest whereby individual caval cannulation and femoral artery perfusion were utilized. Both ventricles were vented, and the aortic root and femoral artery pressure were monitored. Cardioplegia was delivered by means of a calibrated roller pump 250 which calibrates the solution fed from the source 260 and which feeds the solution through a 4° C. water bath 270 into the aortic root. The system for controlling the flow of the solution is controlled by the roller pump.

Figure 5:
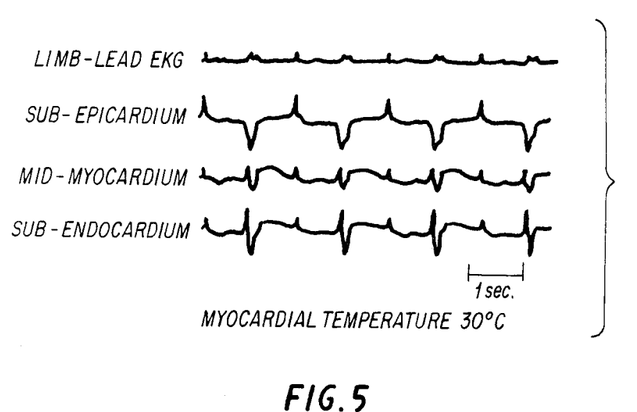
FIG. 5 illustrates control data obtained from normal EKG as well as the data acquisition system of FIG. 1 prior to cardioplegic arrest at a temperature of 30° C.

The FIGS. 5–9 illustrate the results of the comparison of an arrangement using a monitor 100 and the systems of FIGS. 1–3 modified for gain control when compared with a normal 3 limb-lead EKG. The FIG. 5 illustrates the control data which are obtained prior to elective cardioplegic arrest. During the initial set up phase as recorded in the FIG. 5, prior to cardioplegic, arrest the EKG reading indicates normal activity with the 3 intramural electrograms representative of recordings from a plunge needle electrode in the ventricular septum. More specifically, each one of the three readings from the sub-epicardium, the mid-myocardium and the sub-endocardium represent one of the five contact points from each of the three plunge electrodes 20, 30 and 40. At this point the control gain and the slope detecting portions of the monitor 100 are set similar to measurements of the UPPA voltages previously discussed. The temperature is recorded at 30° C. and the system is then prepared for cardioplegic arrest through the manner indicated in FIG. 4. The results of the electrocardiogram and the intramural electrode readings in the ventricle immediately following cardioplegic arrest are shown in the FIG. 6. At this time the gain on the output of the unipolar electrograms has been increased by a factor of 10 over the control gain illustrated in the FIG. 5. This is accomplished in the monitor 100 by adjusting the gain on the follower amplifier 120 and the comparator 145 of the slope detector 140 has its reference voltage at the input 146 adjusted so that practically all electrical activity is detected. In other words, in the previous set up for detecting UPPA voltages the reference input 146 to the comparator 145 of the slope detector 140 was adjusted to provide only for detection of signals which were negative going and more rapid than 2 millivolts per milliseconds. Effectively this limitation has been removed for purposes of detecting the low amplitude activity that may occur during cardioplegic arrest.

Figure 6:
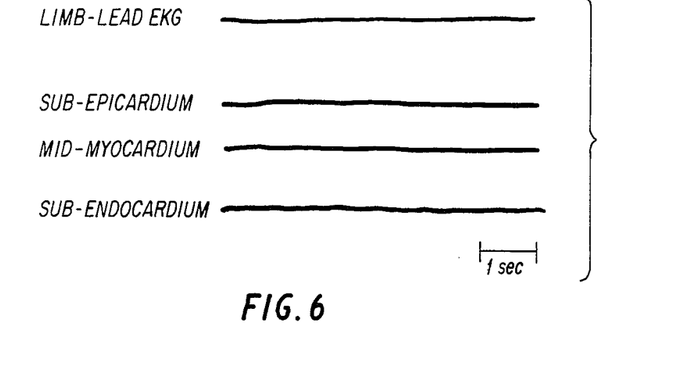
FIG. 6 illustrates the electrical quiescence immediately following cardioplegic arrest including hypothermic arrest and topical cooling to a ventricular septal and free-wall temperature of 10° C.

FIG. 6 illustrates a condition where the myocardial temperature has been reduced to 10° C. and the cardioplegia infusion and the application of topical hypotherma has been accomplished. During this time period total electromechanical arrest has been attained and both the EKG output and the output from the intramural electrodes indicate electrical quiescence.

Figure 7:
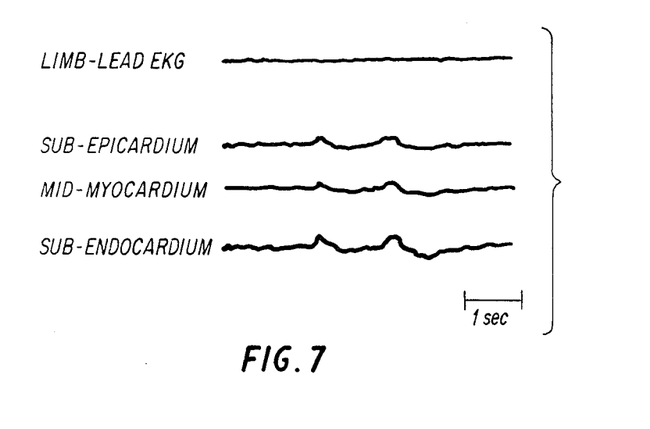
FIG. 7 illustrates initial ventricular electrical activity.

The first ventricular electrical activity made its presence known in the intramural needle electrodes approximately 13 minutes after the initiation of cardioplegic arrest as illustrated in the FIG. 7. It is especially noteworthy that the EKG measurement indicates quiescence at this point so for all practical purposes without the measurements from the gain control adjusted system of FIGS. 1–3 there would be no indication of electrical activity and no visual movement of the heart. Thus, under normal conditions, despite the obvious electrical activity of the heart indicated by the intramural needle electrode outputs from the sub-epicardium, mid-myocardium and the sub-endocardium as reflected by the FIG. 7, the prior processes would not have indicated activity. Once again it is emphasized that at the time this ventricular activity was recorded the electrocardiogram was quiescent and the myocardial temperature was 11° C.

Figure 8:
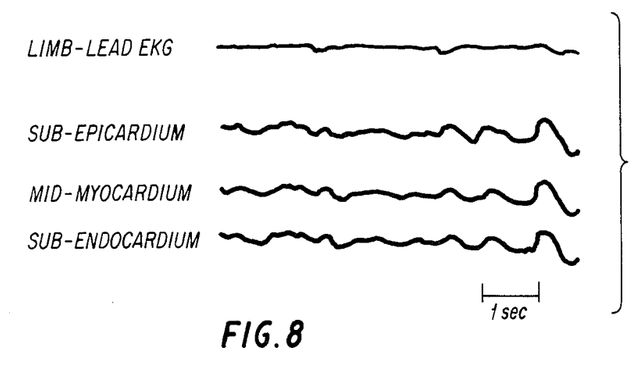
FIG. 8 illustrates continuous ventricular electrical activity.

The intramural ventricular electrical activity becomes more prominent with increasing aortic cross-clamp time despite a regional myocardial temperature of 11° C. as indicated in the FIG. 8. Once again, the presence of this activity is not reflected by the limb-lead electrocardiogram and is not accompanied by any visually discernable mechanical activity. Several minutes after the onset of this intramural electrical activity, slow rhythmic mechanical contractions of the ventricle began which was always accompanied by electrical depolarizations on the limb-lead EKG, but the EKG never had any occurrences during the absence of visual mechanical activity.

Figure 9:
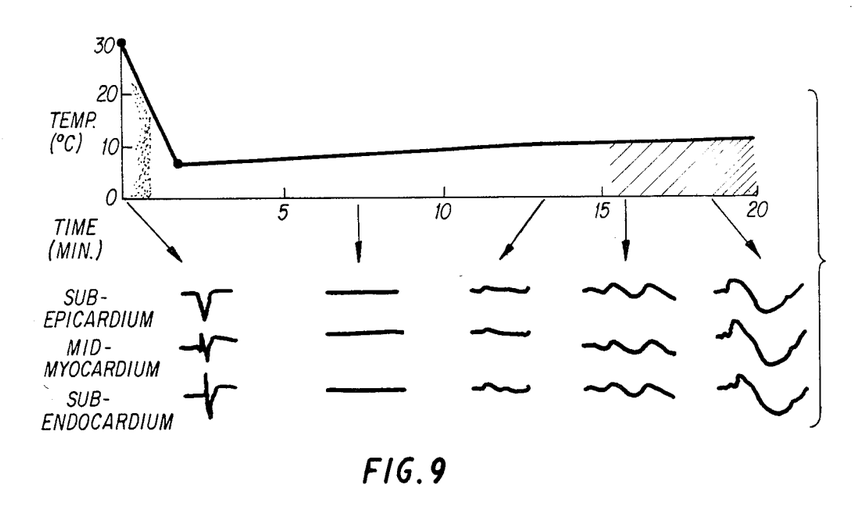
FIG. 9 is a chart illustrating the progression of ventricular electrical activity as a function of myocardial temperature and aortic cross-clamp duration.

Statistical evaluation of experiments on a group of animals indicated that complete electrical quiescence occurred at approximately 0.8 minutes after aortic cross-clamping and cardioplegia infusion and this quiescence persisted for approximately 13 minutes as indicated in FIG. 9. Intramural ventricular electrical activity was first detected at approximately 13.8 minutes after aortic cross-clamping however it was not detected by the limb-lead EKG until 5 minutes later than the first detected intramural ventricular electrical activity. The myocardial temperatures at which this activity occurred had been considered previously to be safe. The development and progression of the previously undetected intramural electrical activity appears to be relatively independent of regional myocardial temperatures as indicated in the FIG. 9.

Thus the use of the monitoring system of FIGS. 1–3, adjusted for gain, can be used to document the return of intramural electrical activity in ventricular myocardium during the period of cardioplegic arrest which is not detectable on a peripheral limb-lead EKG and is not associated with any detectable electromechanical activity and which occurs at temperatures below those previously considered to be adequate for myocardial protection. As previously indicated, clinical studies have shown that there is a direct correlation between the presence of this intramural activity in patients undergoing cardiac surgery and their requirements for postoperative pharmacological and mechanical support.

The optimal treatment of ventricular intramural electrical activity during the period of cardioplegic arrest depends not only on its accurate detection but also on understanding its source of origin so that routine measures may be instituted to prevent its occurrence. Present studies indicate and suggest that after a period of elective cardioplegic arrest the intramural ventricular activity is induced by impulses arising in the lower atrial septum rather than by electrical activity arising de novo in the ventricular myocardium. It has been observed that following the attainment of uniform cardiac electromechanical quiescence by cold cardioplegic infusion, the earliest electrical activity recorded on any of the electrograms always occurred in the lower atrial septum. The studies also seem to indicate that this lower atrial septal activity occurs because of early rewarming of the atrial septum during the period of cardioplegic arrest. Because the AV node resides in the lower interatrial septum, it also rewarms early during cardioplegic arrest and eventually becomes capable of conducting the impulses arising in the lower atrial septum to the ventricles. A short time after the atrial septal impulses were noted, the intramural ventricular electrical activity invariably became diffuse and continuous despite regional myocardial temperatures of 10°–12° C. Thus, if aggressive techniques are employed during cardioplegic arrest to assure adequate atrial and AV node hypothermia, the type of intramural ventricular electrical activity detected can be avoided.

It is to be noted that the very same arrangement of needle electrodes and contact electrodes which are used to determine the unipolar peak-peak amplitude voltages (UPPA) for monitoring myocardial ischemic injury can be used to detect the electrical activity occurring in the heart during the elective cardioplegic arrest portion of the surgery. The only requirements are that the amplifier and the slope detector be modified for the type of signal to be detected including at least a 10-fold gain of the follower amplifier 120 for each of the channels being used. Likewise, of course, the output status of the monitor 100 which is fed to the digital computer must be modified in terms of software modifications in order to provide a different type of indication of activity. Primarily during the cardioplegic arrest portion the output is to be detected for any kind of electrical activity rather than the analysis of the data which occurs in conjunction with detecting UPPA voltages both during and after surgery with the exception of the period of cardioplegic arrest.

Obviously, numerous additional modifications and variations of the present invention are possible in light of the above teachings including the use of such a monitoring system to detect the acute effects on intramural electrophysiology occurring during ventricular cryosurgery during which the system could be used to localize and monitor the intramural progression of ventricular cryolesions during cryothermia applications. It is therfore to be understood that within the scope of the appended claims, the invention may be practiced otherwise than as specifically described herein.

What is claimed as new and desired to be secured by Letters Patent of the United States is:

1. A process for the on-line monitoring of the viability of myocardial tissue of a patient during and after a surgical procedure comprising the steps of:
   implanting multiple electrodes in said tissue prior to said surgical procedure;
   sensing the instantaneous unipolar electrical potentials of said electrodes prior to said surgical procedure;
   registering the peak-to-peak voltage values of said instantaneous unipolar electrical potentials for a period of time occurring prior to said surgical procedure for each of said electrodes which have a negative slope exceeding a predetermined value performing said surgical procedure;

sensing the instantaneous unipolar electrical potentials which have a negative slope exceeding said predetermined value of each of said electrodes during and after said surgical procedure;

comparing said registered values for each of said electrodes with said sensed potentials during and after surgery for each of said electrodes; and providing an output indication of injured tissue when said registered values exceed said sensed potentials during and after surgery by a predetermined amount for at least one of said electrodes.

2. A method according to claim 1 wherein said multiple electrode are plunge electrodes each containing at least one intramural unipolar contact electrode wherein one of said plunge electrodes is implanted in the right ventricle, wherein a second of said plunge electrodes is implanted in the anterior left ventricle, wherein a third of said plunge electrodes is implanted in the lateral left ventricle and wherein a fourth one of said plunge electrodes is implanted in the posterior left ventricle.

3. A method according to claim 2 wherein said second, third and fourth plunge electrode each contain five intramural contact unipolar electrodes.

4. An apparatus for the on-line monitoring of and displaying of the viability of myocardial tissue comprising:

a plurality of electrodes suitable for implantation in said myocardial tissue;

means for sensing the instantaneous electrical potentials of each of said electrodes including a gain control means and a slope detector means wherein said sensing means outputs an amplitude measurement signal when the slope of said instantaneous sensed potential of said electrodes exceeds a predetermined negative value;

means for storing the peak-to-peak amplitude of said signals output from said sensing means for each of said electrodes during a controlled period when said plurality of electrodes are implanted in said myocardial tissue and said myocardial tissue is determined to be healthy tissue;

means for comparing the peak-to-peak amplitude of said signals output from said sensing means with said stored amplitudes wherein said comparator means outputs an indication signal indicating injured tissue when the output of said sensing means is less than a predetermined fraction of said stored values for at least one of said electrodes.

5. An apparatus according to claim 4 wherein said predetermined negative value is 0 and said control time period is 0 and further including a display means for displaying the outputs of said sensing means.

6. An apparatus according to claim 4 wherein said plurality of electrodes comprise a plurality of plunge electrodes each containing at least one intramural unipolar contact electrode.

7. The apparatus according to claim 4 wherein said sensing means further includes a sample and hold circuit for receiving the output of said gain control means and said slope detector means and wherein said sensing means further includes a first delay means connected between the output of said slope detector and said sample and hold means in order to provide for blocking of a subsequent retriggering of said sample and hold circuit during a first predetermined time and a second delay means connected between said slope detector means and said sample and hold circuit in order to provide for a delay of the output of said sample and hold circuit by a second predetermined time in order to provide for continued digitization of signals after a first occurring signal.

8. An apparatus according to claim 7 wherein the output of said sample and hold means is fed to a analog to digital converter with the output of said analog to digital converter providing an 8 bit serial-parallel output to an address generating means.

9. An apparatus according to claim 8 wherein the output of said address generator means is converted by an output circuit means to provide said sensing means outputs and wherein said sensing means outputs are interfaceable with a digital computer.

10. A process for accessing the status of myocardial preservation during cardioplegic arrest in order to assure complete electromechanical arrest from the onset of the application of standard cardioplegic techniques, comprising the steps of:

implanting multiple electrodes in the ventricle of the heart of a patient prior to the initiation of standard cardioplegic techniques;

sensing and recording the output of said multiple electrodes prior to the application of standard cardioplegic techniques;

applying standard cardioplegic techniques to said patient;

sensing and recording the output of said multiple electrodes during the application of said cardioplegic techniques; and providing an output indication of the persistent ventricular activity when signals are sensed during the application of said cardioplegic techniques.

* * * * *